United States Patent [19]

Hsieh

[11] Patent Number: 5,708,690
[45] Date of Patent: Jan. 13, 1998

[54] METHODS AND APPARATUS FOR HELICAL IMAGE RECONSTRUCTION IN A COMPUTED TOMOGRAPHY FLUORO SYSTEM

[75] Inventor: Jiang Hsieh, Waukesha, Wis.

[73] Assignee: General Electric Company, Milwaukee, Wis.

[21] Appl. No.: 729,435

[22] Filed: Oct. 11, 1996

[51] Int. Cl.$^6$ .................................................. A61B 6/03
[52] U.S. Cl. ............................ 378/4; 378/15; 378/901
[58] Field of Search ............................ 378/4, 15, 901

[56] References Cited

U.S. PATENT DOCUMENTS

| | | | |
|---|---|---|---|
| 4,275,444 | 6/1981 | Ryan | 128/653.1 |
| 4,590,582 | 5/1986 | Umemura | 364/724.05 |

Primary Examiner—David P. Porta
Assistant Examiner—David Vernon Bruce
Attorney, Agent, or Firm—John S. Beulick; John H. Pilarski

[57] ABSTRACT

The present invention, in one form, is a system for performing image reconstruction from projection data acquired in a helical scan. More specifically, the system implements an incremental reconstruction algorithm for helical scan projection data which does not require filtering, weighting and backprojecting such projection data for generating each image. Particularly, an overscan weighting algorithm generates weighting factors to be applied to projection data to generate base image projection data. An update weighting algorithm generates update weighting factors to be applied to the base image projection data to generate subsequent image projection data.

14 Claims, 2 Drawing Sheets

METHODS AND APPARATUS FOR HELICAL IMAGE RECONSTRUCTION IN A COMPUTED TOMOGRAPHY FLUORO SYSTEM

FIELD OF THE INVENTION

This invention relates generally to computed tomography (CT) imaging and more particularly, to image reconstruction in a CT fluoroscopic system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Certain reconstruction process steps are known to produce noise structures in an image. For example, and during a "cine" scan, i.e., a scan in which the patient remains stationary while the data for the prescribed number of slices is acquired, underscan weighting ("USW") is employed to reduce motion artifacts that result when patient anatomy moves during the scan. Underscan weighting algorithms typically weight the collected data as a function of view angle and detector channel index. Specifically, prior to filtered back projection, the data is weighted according to a helical weighting factor, which is a function of both the view angle and detector angle. Particularly, projection data is first filtered, then weighted, and subsequently backprojected to generate each image.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighting ("HW") algorithms which weight the collected data as a function of view angle and detector channel index. Specifically, prior to filtered back projection, the data is weighted according to a helical weighting factor, which is a function of both the view angle and detector angle. As with underscan weighting, in a HW algorithm, projection data is filtered, weighted, and backprojected to generate each image.

In a cine scan context and a helical scan context, the same projection data is repeatedly filtered, weighted, and backprojected even though it is continually assigned the same weight. For example, projection data $P_1$ may be weighted $w_1$ to generate a first image $I_1$, and also weighted $w_1$ to generate a second image $I_2$. However, second image $I_2$ cannot be generated without re-filtering, re-weighting and re-backprojecting projection data $P_1$. The underscan weighting algorithms and the helical weighting algorithms both require each image $I_1$ and $I_2$ to be independently generated from projection data $P_1$. Therefore, significant computational redundance occurs with both helical weighting algorithms and underscan weighting algorithms.

Reconstruction techniques for improving certain aspects of image generation are known. For example, overscan weighting is employed to decrease computational redundancy associated with reconstructing overlapping images with projection data. Particularly, in overscan weighting, the collected projection data is weighted only as a function of view angle. Therefore, while not eliminating computational redundancy, overscan weighting reduces the computations necessary for image reconstruction. Moreover, overscan weighting is known to reduce motion artifacts that result when patient anatomy moves during a 360 degree CT scan. Patient motion causes views at the beginning and ending projections to be inconsistent and discontinuous. However, while overscan weighting is successful in reducing motion artifacts, overscan weighting may also produce noise structures in the final image and degrades image quality. In helical scanning, the image degradation caused by overscan weighting is typically severe, thus precluding the use of overscan weighting during helical scans.

In CT fluoroscopic systems ("CT Fluoro"), it is known to generate sequential frames of images. A frame, like a view, corresponds to a two dimensional slice taken through the imaged object. Particularly, projection data is processed at a frame rate to construct an image frame of the object. Typically, projection data is not weighted so that the frame rate may be increased. However, non-weighted projection data is known to produce noticeable shading and streaking in generated images. To reduce such shading and streaking, helical weighting algorithms may be used to weight the projection data corresponding to each frame. However, the more often projection data is filtered, weighted and backprojected, the slower the frame rate. The frame rate is thus limited to the computational capabilities of the CT Fluoro system.

It would be desirable, of course, to decrease computational redundancy in helical scan image reconstruction. It also would be desirable to facilitate the reduction of artifacts and offer reasonable trade-offs between artifact reduction and frame rate in CT fluoroscopic helical image reconstruction.

SUMMARY OF THE INVENTION

These and other objects may be attained in a system which, in one embodiment, implements an incremental reconstruction algorithm for helical scan projection data which does not require filtering, weighting and backprojecting all projection data for generation of each image. Particularly, and in accordance with one embodiment of the present invention, an overscan weighting algorithm generates weighting factors to be applied to the projection data to generate base image projection data. For subsequent images, the base image projection data is utilized to generate the image data. Specifically, an update weighting algorithm generates updated weighting factors to be applied to the base image projection data to generate subsequent image projection data.

Using the incremental reconstruction algorithm described above enables reconstruction of subsequent images from helical scan data without requiring that each image be independently generated. Further, the computational costs and expenses of generating images in CT Fluoro helical image reconstruction are reduced. Such algorithm also decreases the processing time and offers reasonable trade-offs between artifact reduction and frame rate. In addition, the present image algorithm is not believed to significantly decrease image quality.

DETAILED DESCRIPTION OF THE DRAWINGS

Figure 1:
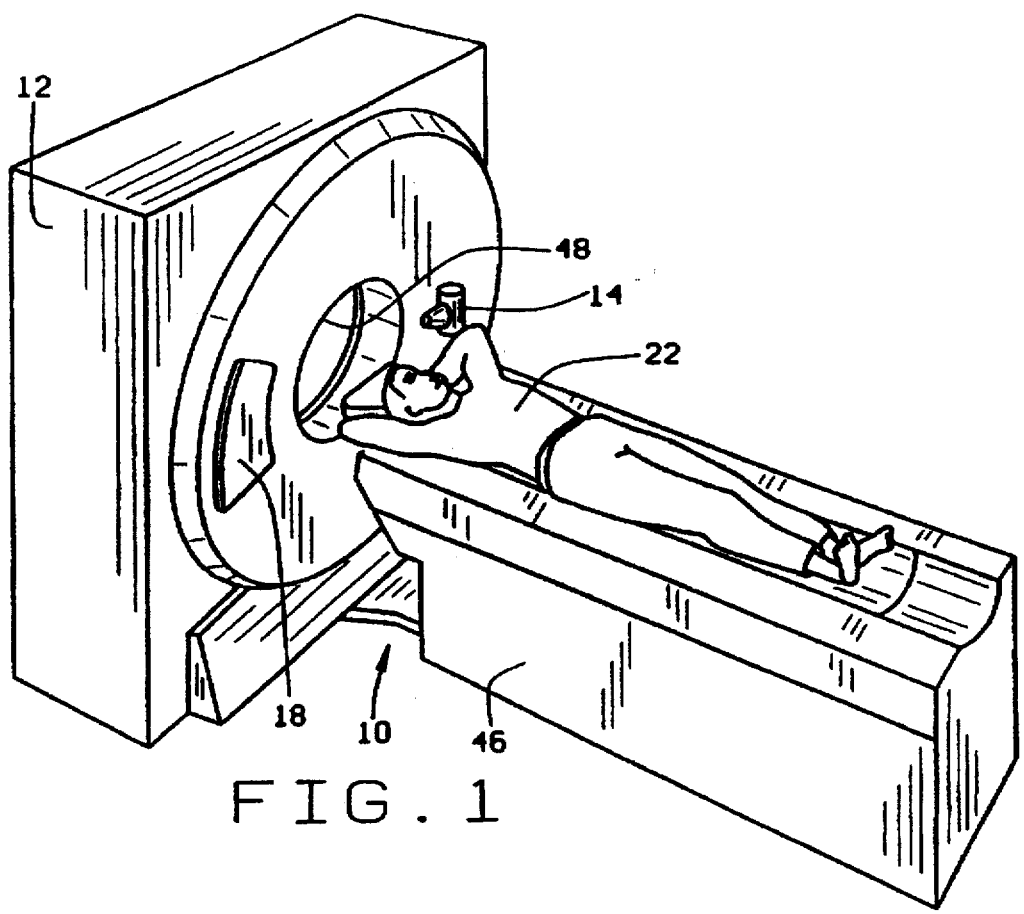
FIG. 1 is a pictorial view of a CT imaging system.
Figure 2:
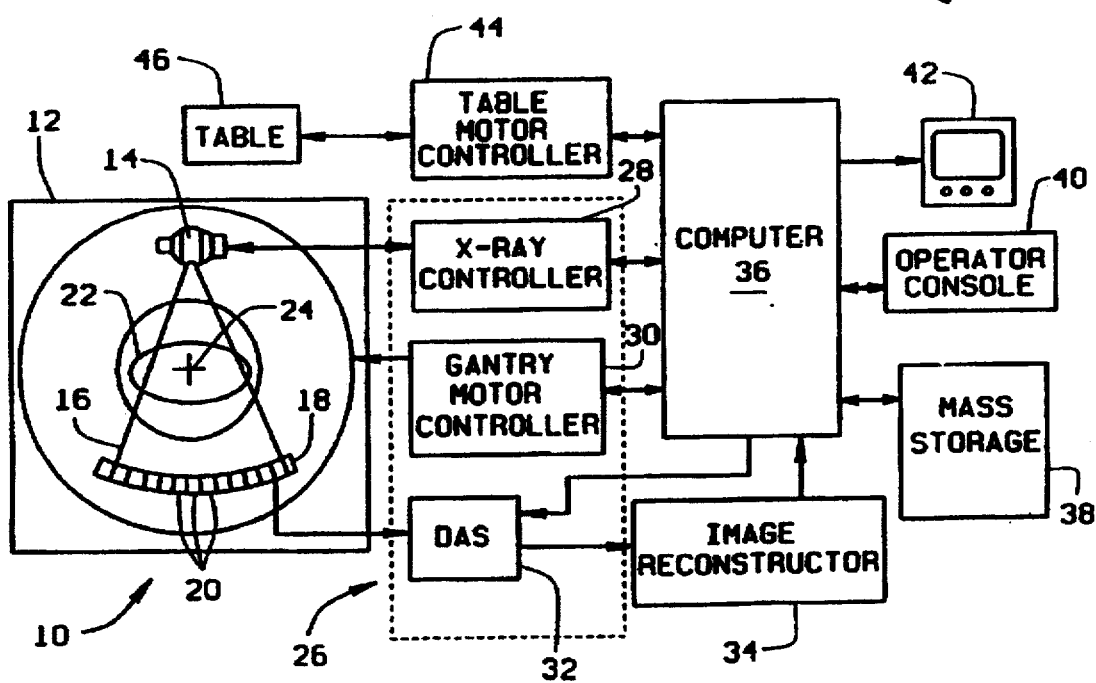
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on, i.e., dependent upon, both the fan angle and view angle. While the HE and HI algorithms provides generally acceptable image quality, such algorithms employ significant computational redundancies, and require significant hardware costs when reconstruction speed is crucial. For example, almost all projections that are used to generate an original image will have to be re-weighted, re-filtered, and re-backprojected to generate a new image that is even a small fraction of the rotation apart. Particularly, even where a significant mount of overlap occurs in projections of sequential images, to generate n images per gantry rotation, n times the mount of computation that is needed to generate a single image is needed during the gantry rotation.

The following discussion of an overscan weighting algorithm and an update weighting algorithm sometimes refers specifically to CT Fluoro systems using a helical scan or a cine scan. The overscan weighting algorithm and update algorithm, however, are not limited to practice in connection with such systems, and may be used with other CT systems. Further, in one embodiment, the overscan weighting algorithm and update algorithm would be implemented in computer 36 and would process, for example, data stored in mass storage 38. Many other alternative implementations are, of course, possible.

In accordance with one embodiment of the present invention, overscan weighting is used to generate base image data for a base image. Specifically, to generate the base image, gantry 12 rotates one full revolution plus a view angle of $\beta_0$, i.e., over the range $(0, 2\pi+\beta_0)$, to acquire projection data. Angle $\beta_0$ represents the angle of gantry rotation in excess of 360° during a helical scan. The filtered projection data acquired during the helical scan is then weighted using an overscan weighting algorithm. The overscan weighting algorithm applies a weighting factor $w(\beta)$ to the projection data acquired at different view angles $\beta$. In one embodiment, the weighting factor $w(\beta)$ is:

$$w(\beta) = 3x^2(\beta) - 2x^3(\beta), \tag{1}$$

where:

$$x(\beta) = \begin{cases} \dfrac{\beta}{\beta_0} & 0 \leq \beta \leq \beta_0, \\ 1 & \beta_0 \leq \beta \leq 2\pi, \text{ and} \\ \dfrac{2\pi + \beta_0 - \beta}{\beta_0} & 2\pi \leq \beta \leq 2\pi + \beta_0. \end{cases}$$

Each generated weighting factor is applied to the projection data to generate base image projection data for a base image. Particularly, the filtered projection data is multiplied by the generated weighting factor, and then backprojected.

An update weighting algorithm is then applied to the base image projection data to generate subsequent images.

Particularly, a view angle, 86, for a first projection of a subsequent image is selected. Projection data contributing to the subsequent image is in the range $(\xi, 2\pi+\xi+\beta_0)$. By executing the update weighting algorithm, an updated weighting factor based on each view angle, $\beta$, and an overscan weighting factor $w(\beta)$ within the range $(\xi, 2\pi+\xi+\beta_0)$ is generated. Specifically, update weighting algorithm determines an updated weighting factor to apply to previously filtered, weighted, and backprojected base image projection data so that the subsequent image is generated without re-filtering, re-weighting and re-backprojecting all of the base image projection data.

Figure 3A:
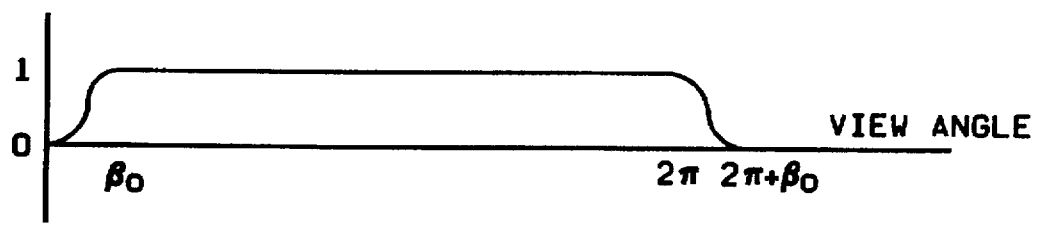
FIG. 3a is a graph illustrating overscan weighting factors versus view angle for generating a first image in accordance with one embodiment of the present invention.
Figure 3B:
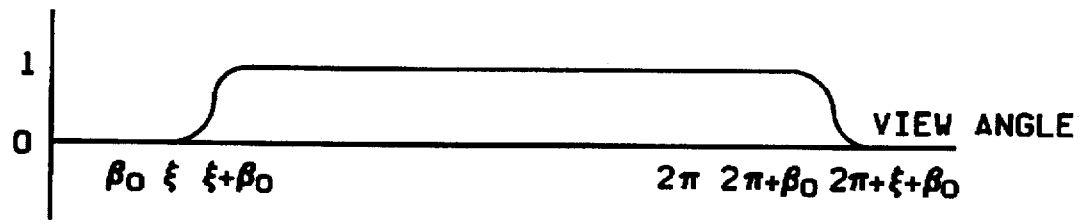
FIG. 3b is a graph illustrating overscan weighting factors versus view angle for generating a second image in accordance with one embodiment of the present invention.
Figure 3C:
FIG. 3c is a graph illustrating updated weighting factors versus view angle for generating a second image in accordance with one embodiment of the present invention.

FIG. 3a, for example, is a graph illustrating overscan weighting factors versus view angle for generating a first image in accordance with one embodiment of the present invention. FIG. 3b is a graph illustrating overscan weighting factors versus view angle for generating a subsequent image, wherein the subsequent image begins at view angle $\xi$. Particularly, $\xi$ represents the view angle at which the first projection of the subsequent image is located, and the curve illustrates the weights applied to projection data for the generation of the subsequent image. FIG. 3c is a graph illustrating update weighting factor versus view angle for generating a subsequent image in accordance with one embodiment of the present invention. As shown, the updated weighting factors correspond to the differences between overscan weighting factors applied to projection data for the base image and to the same projection data for the subsequent image. Update weighting factors are thus applied directly to the previously filtered and weighted base image projection data (FIG. 3a) to generate the appropriate contribution of such projection data (FIG. 3b) to the subsequent image.

respect to projection data in the range $(\xi+\beta_0, 2\pi)$. Therefore, the update weighting algorithm generates weighting factors having a value of zero within this range. Specifically, the previously filtered, weighted and backprojected base image projection data is simply re-used to generate the subsequent image. Conversely, the overscan weighting factors applied to projection data in the ranges $(0,\xi+\beta_0)$ and $(2\pi,2\pi+\xi+\beta_0)$ differ between the first image and the subsequent image. The update weighting algorithm thus generates non-zero update weighting factors within these ranges. More particularly, the update weighting algorithm generates updated weighting factors which, when applied to the base image projection data, re-weights the base image projection data so that the base data contribution to the subsequent image is in accordance with the overscan weighting factors illustrated in FIG. 3b. However, such base image projection data is not re-filtered. Therefore, a substantial portion of the subsequent image is generated without re-filtering, re-weighting, or re-backprojecting the previously acquired base image projection data. Accordingly, significant amounts of filtering, multiplication, and back projection are eliminated, thus improving the computational efficiency of the system. More specifically, the only projection data required to be filtered to generate the subsequent image is projection data previously not filtered for generating the base image projection data. As shown in FIG. 3c, this is not a substantial amount of data.

The update weighting algorithm varies depending upon whether $\xi<\beta_0$ or $\xi\geq\beta_0$. Particularly, where $f(\beta)$ indicates the overscan weights for the region $(0,\beta_0)$, then the update weighting factors $F(\beta)$ used to generated the k-th image (where k=0 for the base image) when $\xi\geq\beta_0$ are:

$$F(\beta) = \begin{cases} -f\left[\dfrac{\beta-(k-1)\xi}{\beta_0}\right] & (k-1)\xi \leq \beta < (k-1)\xi+\beta_0, \\ -1 & (k-1)\xi+\beta_0 \leq \beta \leq k\xi, \\ f\left[\dfrac{\beta-k\xi}{\beta_0}\right]-1 & k\xi < \beta < k\xi+\beta_0, \\ 1-f\left[\dfrac{2\pi+(k-1)\xi+\beta_0-\beta}{\beta_0}\right] & 2\pi+(k-1)\xi < \beta < 2\pi+(k-1)\xi+\beta_0, \\ 1 & 2\pi+(k-1)\xi+\beta_0 \leq \beta \leq 2\pi+k\xi, \\ f\left[\dfrac{2\pi+k\xi+\beta_0-\beta}{\beta_0}\right] & 2\pi+k\xi < \beta < 2\pi+k\xi+\beta_0, \text{ and} \\ 0 & \text{otherwise.} \end{cases} \quad (3)$$

As shown in FIG. 3c, the overscan weighting factors are the same for both the first and subsequent images with The update weighting factors $F(\beta)$ used to generate the k-th image when $\xi<\beta_0$ are:

$$F(\beta) = \begin{cases} -f\left[\dfrac{\beta-(k-1)\xi}{\beta_0}\right] & (k-1)\xi \leq \beta < k\xi, \\[4pt] f\left[\dfrac{\beta-k\xi}{\beta_0}\right] - f\left[\dfrac{\beta-(k-1)\xi}{\beta_0}\right] & k\xi < \beta \leq \beta_0 + (k-1)\xi, \\[4pt] f\left[\dfrac{\beta-k\xi}{\beta_0}\right] - 1 & \beta_0 + (k-1)\xi < \beta < k\xi + \beta_0, \\[4pt] 1 - f\left[\dfrac{2\pi+(k-1)\xi+\beta_0-\beta}{\beta_0}\right] & 2\pi+(k-1)\xi < \beta < 2\pi + k\xi, \\[4pt] f\left[\dfrac{\beta_0+2\pi+k\xi-\beta}{\beta_0}\right] - f\left[\dfrac{\beta_0+2\pi+(k-1)\xi-\beta}{\beta_0}\right] & 2\pi+k\xi \leq \beta \leq 2\pi+\beta_0+(k-1)\xi, \\[4pt] f\left[\dfrac{2\pi+k\xi+\beta_0-\beta}{\beta_0}\right] & 2\pi+(k-1)\xi+\beta_0 < \beta < 2\pi+k\xi+\beta_0, \\[4pt] 0 & \text{otherwise.} \end{cases}$$

The weighting factor $F(\beta)$ is then applied to the projection data to generate an image.

As one specific example, and where $\beta_0=\xi=\pi/4$, only 123 additional views (out of 984) in the view angle range $(2.25\pi, 2.5\pi)$ are filtered to generate a subsequent image. Views in the ranges $(0, 0.5\pi)$ and $(2\pi, 2.5\pi)$ need only be re-weighted with the update weighting factors and re-backprojected. Moreover, and because the views in the ranges $(0, 0.5\pi)$ and $(2\pi, 2.5\pi)$ are one revolution apart, the weighted projections may first be combined before filtering and backprojecting. However, the views in the range $(0.5\pi, 2\pi)$ are neither re-filtered, re-weighted, nor re-backprojected. Therefore, only approximately ⅛ of the projection data set needs to be filtered and only approximately ¼ of the views need to be backprojected to obtain the subsequent image.

The values of both $\beta_0$ and $\xi$, above, are $\pi/4$. However, $\beta_0$ and $\xi$ may have other values, and need not be the same value. Similarly, the values of $\beta_0$ and $\xi$ may be selected and stored, for example, in computer 36. Alternatively, of course, such values may be selected at the final stage of image quality evaluation.

The value of $\beta_0$ is closely related to the computational efficiency and the image quality of the CT Fluoro system. Particularly, a smaller value of $\beta_0$ typically provides a better computation efficiency, since the number of views that need to be filtered and the number of views that need to be backprojected are directly linked to $\beta_0$. However, if $\beta_0$ is too small, the CT Fluoro system artifact suppression capability will be degraded, thus degrading the image quality.

The value of $\xi$, alternatively, is closely related to the desired frame rate of the CT Fluoro system. Particularly, the higher the frame rate, the smaller the value of $\xi$. However, if a very high frame rate is selected, e.g., 24 frames per revolution, the $\xi$ value will become very small and the computation efficiency will suffer. Therefore, the values of $\beta_0$ and $\xi$ may be modified to trade-off image quality with computational efficiency.

Similarly, the update weighting algorithm may be used in connection with known helical weighting algorithms to trade-off computational efficiency with image quality. Particularly, it is believed that as long as the Nyquist sampling criteria is satisfied in the z direction for the CT Fluoro system, image space interpolation utilized in helical weighting algorithms will not degrade image quality.

The above described algorithm facilitates improving computational efficiency without significantly degrading image quality in CT Fluoro image reconstruction. Such algorithm also decreases the processing time and offers reasonable trade-offs between artifact reduction and frame rate.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a CT Fluoro system. Many other CT systems may be used. Similarly, while the values of $\beta$ and $\xi$ are described herein as being selected as the final stage of image quality evaluation, any or all of these values may be pre-selected and stored in the computer. Furthermore, the overscan weights described are determined in accordance to a linear function, i.e., $w(\beta)$ is proportional to $\beta$. However, the overscan weights may be generated with a non-linear function, or with a different linear function. In addition, while the invention is described in connection with a helical scan, the invention may also be used in connection with a cine scan. Accordingly, the spirit and scope of the invention are to be limited only by the terms of the appended claims.

What is claimed is:

1. A system for producing a base tomographic image and a subsequent tomographic image of an object using projection data acquired in a scan, said system comprising an x-ray source and a detector array, said detector array comprising a plurality of detectors, said system configured to:

apply an overscan weighting algorithm to the projection data to generate base image projection data;

determine a subsequent image view angle; and apply an update weighting algorithm to the base image projection data, using the determined subsequent image view angle, to generate subsequent image projection data.

2. A system in accordance with claim 1 wherein the overscan weighing algorithm is:

$$w(\beta)=3x^2(\beta)-2x^3(\beta),$$

where:

$$x(\beta) = \begin{cases} \dfrac{\beta}{\beta_0} & 0 \leq \beta \leq \beta_0, \\ 1 & \beta_0 \leq \beta \leq 2\pi, \text{ and} \\ \dfrac{2\pi + \beta_0 - \beta}{\beta_0} & 2\pi \leq \beta \leq 2\pi + \beta_0; \end{cases}$$

$\beta$ is a view angle;

$\beta_0$ is an angle of gantry rotation in excess of 360° during a helical scan;

$x(\beta)$ is a weighting function; and $w(\beta)$ is an overscan weighting factor corresponding to view angle $\beta$.

3. A system in accordance with claim 1 wherein the update weighting algorithm $F(\beta)$ is:

$$F(\beta) = \begin{cases} -f\left[\dfrac{\beta - (k-1)\xi}{\beta_0}\right] & (k-1)\xi \leq \beta < (k-1)\xi + \beta_0, \\ -1 & (k-1)\xi + \beta_0 \leq \beta \leq k\xi, \\ f\left[\dfrac{\beta - k\xi}{\beta_0}\right] - 1 & k\xi < \beta < k\xi + \beta_0, \\ 1 - f\left[\dfrac{2\pi + (k-1)\xi + \beta_0 - \beta}{\beta_0}\right] & 2\pi + (k-1)\xi < \beta < 2\pi + (k-1)\xi + \beta_0, \\ 1 & 2\pi + (k-1)\xi + \beta_0 \leq \beta \leq 2\pi + k\xi, \\ f\left[\dfrac{2\pi + k\xi + \beta_0 - \beta}{\beta_0}\right] & 2\pi + k\xi < \beta < 2\pi + k\xi + \beta_0, \text{ and} \\ 0 & \text{otherwise} \end{cases}$$

where $\xi \geq \beta_0$, and $$F(\beta) = \begin{cases} -f\left[\dfrac{\beta - (k-1)\xi}{\beta_0}\right] & (k-1)\xi \leq \beta < k\xi, \\ f\left[\dfrac{\beta - k\xi}{\beta_0}\right] - f\left[\dfrac{\beta - (k-1)\xi}{\beta_0}\right] & k\xi < \beta \leq \beta_0 + (k-1)\xi, \\ f\left[\dfrac{\beta - k\xi}{\beta_0}\right] - 1 & \beta_0 + (k-1)\xi < \beta < k\xi + \beta_0, \\ 1 - f\left[\dfrac{2\pi + (k-1)\xi + \beta_0 - \beta}{\beta_0}\right] & 2\pi + (k-1)\xi < \beta < 2\pi + k\xi, \\ f\left[\dfrac{\beta_0 + 2\pi + k\xi - \beta}{\beta_0}\right] - f\left[\dfrac{\beta_0 + 2\pi + (k-1)\xi - \beta}{\beta_0}\right] & 2\pi + k\xi \leq \beta \leq 2\pi + \beta_0 + (k-1)\xi, \\ f\left[\dfrac{2\pi + k\xi + \beta_0 - \beta}{\beta_0}\right] & 2\pi + (k-1)\xi + \beta_0 < \beta < 2\pi + k\xi + \beta_0, \\ 0 & \text{otherwise} \end{cases}$$

where $\xi < \beta_0$; and
where:

$\beta$ is a view angle;

$\beta_0$ is an angle of gantry rotation in excess of 360° during a scan;

$k$ is a numbered image to be generated;

$f(\beta)$ indicates overscan weights for a region $(0, \beta_0)$; and $\xi$ is the subsequent image view angle.

4. A system in accordance with claim 3 wherein $\xi = \pi/4$.

5. A system in accordance with claim 3 wherein $\beta_0 = \pi/4$.

6. A system in accordance with claim 3 further comprising a computer having a memory, and wherein values for $\xi$ and $\beta_0$ are stored in said memory.

7. A system in accordance with claim 1 further configured to combine projection data that is one gantry revolution apart.

8. A method for reconstructing an image of an object in a CT system using projection data acquired in a scan, the CT system having an x-ray source for projecting x-rays and a detector array, said detector array comprising a plurality of detectors, said method comprising the steps of:

applying an overscan weighting algorithm to the projection data to generate base image projection data; and applying an update weighting algorithm to the base image projection data to generate subsequent image projection data.

9. A method in accordance with claim 8 wherein the overscan weighing algorithm is:

$$w(\beta) = 3x^2(\beta) - 2x^3(\beta),$$

where:

$$x(\beta) = \begin{cases} \dfrac{\beta}{\beta_0} & 0 \leq \beta \leq \beta_0, \\ 1 & \beta_0 \leq \beta \leq 2\pi, \text{ and} \\ \dfrac{2\pi + \beta_0 - \beta}{\beta_0} & 2\pi \leq \beta \leq 2\pi + \beta_0; \end{cases}$$

$\beta$ is a view angle;

$\beta_0$ is an angle of gantry rotation in excess of 360° during a helical scan;

$x(\beta)$ is a weighting function; and $w(\beta)$ is an overscan weighting factor corresponding to view angle $\beta$.

10. A method in accordance with claim 8 wherein the update weighting algorithm $F(\beta)$ is:

$$F(\beta) = \begin{cases} -f\left[\dfrac{\beta - (k-1)\xi}{\beta_0}\right] & (k-1)\xi \leq \beta < (k-1)\xi + \beta_0, \\ -1 & (k-1)\xi + \beta_0 \leq \beta \leq k\xi, \\ f\left[\dfrac{\beta - k\xi}{\beta_0}\right] - 1 & k\xi < \beta < k\xi + \beta_0, \\ 1 - f\left[\dfrac{2\pi + (k-1)\xi + \beta_0 - \beta}{\beta_0}\right] & 2\pi + (k-1)\xi < \beta < 2\pi + (k-1)\xi + \beta_0, \\ 1 & 2\pi + (k-1)\xi + \beta_0 \leq \beta \leq 2\pi + k\xi, \\ f\left[\dfrac{2\pi + k\xi + \beta_0 - \beta}{\beta_0}\right] & 2\pi + k\xi < \beta < 2\pi + k\xi + \beta_0, \text{ and} \\ 0 & \text{otherwise,} \end{cases}$$

where $\xi \geq \beta_0$, and $$F(\beta) = \begin{cases} -f\left[\dfrac{\beta - (k-1)\xi}{\beta_0}\right] & (k-1)\xi \leq \beta < k\xi, \\ f\left[\dfrac{\beta - k\xi}{\beta_0}\right] - f\left[\dfrac{\beta - (k-1)\xi}{\beta_0}\right] & k\xi < \beta \leq \beta_0 + (k-1)\xi, \\ f\left[\dfrac{\beta - k\xi}{\beta_0}\right] - 1 & \beta_0 + (k-1)\xi < \beta < k\xi + \beta_0, \\ 1 - f\left[\dfrac{2\pi + (k-1)\xi + \beta_0 - \beta}{\beta_0}\right] & 2\pi + (k-1)\xi < \beta < 2\pi + k\xi, \\ f\left[\dfrac{\beta_0 + 2\pi + k\xi - \beta}{\beta_0}\right] - f\left[\dfrac{\beta_0 + 2\pi + (k-1)\xi - \beta}{\beta_0}\right] & 2\pi + k\xi \leq \beta \leq 2\pi + \beta_0 + (k-1)\xi, \\ f\left[\dfrac{2\pi + k\xi + \beta_0 - \beta}{\beta_0}\right] & 2\pi + (k-1)\xi + \beta_0 < \beta < 2\pi + k\xi + \beta_0, \\ 0 & \text{otherwise,} \end{cases}$$

where $\xi < \beta_0$; and where:

$\beta$ is a view angle;

$\beta_0$ is an angle of gantry rotation in excess of 360° during a helica 1 scan;

k is a numbered image to be generated;

$f(\beta)$ indicates overscan weights for a region $(0, \beta_0)$; and $\xi$ is the subsequent image view angle.

11. A method in accordance with claim 10 wherein $\xi = \pi/4$.

12. A method in accordance with claim 10 wherein $\beta_0 = \pi/4$.

13. A method in accordance with claim 10 wherein the system further includes a computer having a memory, and wherein said method further comprises the steps of selecting values for $\xi$ and $\beta_0$, and storing the selected values for $\xi$ and $\beta_0$ in the computer memory.

14. A method in accordance with claim 8 further comprising the step of combining projection data that is one gantry revolution apart.

* * * * *